(12) United States Patent
Franz et al.

(10) Patent No.: US 6,395,309 B1
(45) Date of Patent: *May 28, 2002

(54) USE OF AN EXTRACT OF ALCHEMILLA VULGARIS TO INHIBIT ANGIOGENESIS

(75) Inventors: Gerhard Franz, Regensburg; Dietrich H. Paper, Maxhutte-Haidhof, both of (DE)

(73) Assignee: Weber & Weber GmbH & Co. KG (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/381,889

(22) PCT Filed: Mar. 25, 1998

(86) PCT No.: PCT/EP98/01753
§ 371 Date: Dec. 22, 1999
§ 102(e) Date: Dec. 22, 1999

(87) PCT Pub. No.: WO98/42357
PCT Pub. Date: Oct. 1, 1998

(30) Foreign Application Priority Data

Mar. 25, 1998 (DE) .......................... 197 12 659

(51) Int. Cl.⁷ .................. A01N 65/00; A61K 35/78; A61K 39/385
(52) U.S. Cl. .................. 424/725; 514/863; 514/886; 514/914
(58) Field of Search .............. 424/195.1, 725; 514/886, 863, 914

(56) References Cited

U.S. PATENT DOCUMENTS 4,054,649 A    10/1977    Cariel

FOREIGN PATENT DOCUMENTS

FR    2332026    6/1977    .......... A61K/35/78

OTHER PUBLICATIONS

Jonadet et al. J de Pharmacologie, 17 (1). Flavanods extracted from Ribes nigrum L. and Alchemilla vulgarisL.: In vitro inhibitory activites on elastase, trypsin and chymotrypsin–2. Angioprotective activities compared in vivo, 1986 (Abstract included).*
Hoffman, D. The Complete Illustrated Herbal pp20–31 and 56. Barnes & Noble Inc., NY, 1996.*
"Class C homeopathic tinctures of botanical substances 1/10 (10%)", *HPRS—49 General Pharmacy*, 1 page (Sep. 1997).
"Extraction / Extractives", *Pharmaceutical Sciences—Remington's 16th Ed.*, Mack Publishing Co., Easton, PA, 1461–1462 (1980).
"Solidaginis virgaureae herba (Golden Rod)", *ESCOP*, 1 page (Mar. 1996).
Gagliardi, A., et al., "Inhibition of Angiogenesis by Suramin", *Cancer Research*, vol. 52, 5073–5075 (Sep. 15, 1992).
Hahnenberger, R., et al., "Low–sulphated oligosaccharides derived from heparan sulphate inhibit normal angiogenesis", *Glycobiology*, vol. 3, No. 6, 567–573 (1993).
Lewis, C.T., et al., "A Latin Dictionary", Oxford (Clarendon Press); definition on p. 817; 4 pages (1962).
Ribatti, D., et al., "The chick embryo chorioallantoic membrane as a model for in vivo research on anti–angiogenesis", *Current Pharmaceutical Biotechnology*, vol. 1, 73–82 (2000).
Svahn, C.M., et al., "Inhibition of angiogenesis by heparin fragments in the presence of hydrocortisone", *Carabohydrate Polymers*, vol. 18, 9–16 (1992).
Hansel, R., et al., "Drogen A–D", *Hagers Handbuch*, Springer–Verlag Berlin Heidelberg, 9 pages, (1992).

* cited by examiner

*Primary Examiner*—Christopher R. Tate
*Assistant Examiner*—Michele C. Flood
(74) *Attorney, Agent, or Firm*—Schwegman, Lundberg, Woessner & Kluth, P.A.

(57) ABSTRACT

Use of an extract of *alchemilla vulgaris*, or a fraction or a lyophilizate thereof, or one or more active principles contained in said extract, for inhibiting angiogenesis.

18 Claims, No Drawings

USE OF AN EXTRACT OF ALCHEMILLA VULGARIS TO INHIBIT ANGIOGENESIS

The invention concerns a new use of an extract of *Alchemilla vulgaris* or a fraction of it or a lyophilizate of it, or one or more active components of the extract to inhibit angiogenesis.

Extracts of *Alchemilla vulgaris* (lady's mantle) and various pharmacological effects of these extracts are known.

The primary tincture of *Alchemilla vulgaris* is an extract from the Alchemilla herb obtained with 43% (w/w) ethanol. The primary tincture contains tannins of ellagitannin type. The structures of the dimer ellagitannins Agrimoniin, Laevigatin F and Pendunculagin are known. In addition, the primary tincture contains flavanoids, leukocyanidins and caffeic acid derivatives (see Hansel, R., Keller, K., Rimpler, H., Schneider, G. (Publishers), Hager's Handbook, Volume 4, 5th Edition, pp. 161–166, Springer-Verlag, Berlin, Heidelberg, 1992; Ploss, E., Research Material from Phytopharmaceutical Cooperation; *Alchemilla vulgaris* L, lady's mantle, 1985).

Anti-inflammatory effects expressed as inhibition of synthesis of prostaglandins of the cyclooxygenase pathway and spasmolytic effects are known for the flavanoids of the *Herba Alchemille*. Campherol inhibits histamine release from mast cells. Capillary-sealing, antiedematous effects are also described for the flavanoids and leukocyanadins. The hemostyptic tannins can also participate in these effects. The hemostyptic effect of the tannins was detected in animal tests following peroral administration of the *Herba Alchemille*. The tannins also have an astringent effect and, through this, a stimulus-moderating, anti-inflammatory and antisecretory effect on the mucus membranes of the gastrointestinal tract (Ploss, E., op. cit.).

Certain flavanoid fractions from the Herba Alchemille inhibit various proteases from the pancreas, elastase, trypsin and $\alpha$-chymotrypsin, in vitro. These enzymes can injure connective tissues pathophysiologically or even activate enzyme mediators such as the kinins. One thing that is being discussed is a tissue-protective effect due to the protease inhibitions (Jonadet, M., et al, Flavanoid Extracts of *Ribes Nigrum* L. and *Alchemilla vulgaris* L., J. Pharmacol 17, 1, 21–27 (1986)).

No toxic effects of the *Herba Alchemille* are known (Ploss, E., op. cit.).

Because of its anti-inflammatory properties the *Herba Alchemille* is used in diarrheal diseases (Ploss, E., op. cit; *Alchemilla herba*, Monograph of Commission E, BAnz. 173, Sep. 18, 1996). In addition, the drug is used internally for therapeutic cases in menorrhagia and metrorragia due to its spasmolytic and hemostyptic effects (Ploss, E., op. cit.). Other uses are as a gargle solution in cases of inflammations in the mouth and throat and topical use for ulcers (Hansel, R., et al., op. cit.).

Surprisingly, it has now been established that extracts of *Alchemilla vulgaris*, especially lyophilizates thereof, show unexpectedly new pharmacological effects, which neither have been described nor are suggested by the known components and prior indications for the drug.

In accordance with the invention, the invention concerns the use of an extract of *Alchemilla vulgaris*, preferably the primary tincture, or a fraction of it or a lyophilizate thereof, or one or more active components of the extract to inhibit angiogenesis, especially in tumor diseases, rheumatoid arthritis and other chronic inflammatory diseases, psoriases, retinopathies and periodontal inflammations, where this is, however, only an exemplary list and future therapeutic applications are also conceivable in other areas where inhibition of angiogenesis plays a role.

The dosage of the primary tincture dry substance lies especially preferably between 20 mg and 2 g per day.

In accordance with the invention, dragées, hard gelatin capsules, liquid preparations of the primary tincture dry substance as oral medicines, topical drugs or injectable substances are preferably used as administration forms.

The primary intent is for use in humans, but use in veterinary medicine is also possible.

The new pharmacological effects have been confirmed by the proved inhibition of angiogenesis in the chorioallantoic membrane (CAM) of the incubated hen's egg by a lyophilizate of the primary tincture of *Alchemilla vulgaris*, as specified above in more detail. Here 10 $\mu$L or a solution of 50 mg lyophilizate in 1 mL agarose solution was administered to the CAM as a test pellet. In the region of the test pellet the capillary density was seen to be lower than in the control test up to the point of complete suppression of angiogenesis, where it was seen as a capillary-free background. This test setup is a recognized model for in vitro testing of the inhibition of angiogenesis and confirms the completely unexpected, novel pharmacological effects of the said lyophilizates.

This CAM test is one of a series of model tests to check substances for their angiogenesis-inhibiting effect for possible therapeutic applications. The advantage of the CAM test is that it belongs to the in vivo tests which allow a more reliable statement of clinical relevance than in vitro processes. In this in vivo test the complex system of angiogenesis occurs with all of its cell functions and mediators, so that a comparably reliable statement on the inhibition of angiogenesis is possible. The test is recognized as a screening process for determining substances with angiogenesis-inhibiting properties (Svahn, C. M., M. Weber, C. Mattsson, K. Neiger, M. Palm Carbohydr. Polym. 18, 9–16 (1992); Hahnenberger, R., A. M. Jakobsen, A. Ansari, T. Wehler, C. M. Svahn, U. Lindahhl, Glycobiology 3, 567–573 (1993); and Galdiardi, A., H. Hadd, D. C. Collins, Cancer Res. 52, 5073–5075 (1992)).

Angiogenesis is a physiological tissue differentiation process that occurs in embryonic development, after menstruation and in wound healing. This differentiation begins with capillaries, in which the basal membrane becomes loosened from place to place, endothelial cells migrate and proliferate, join together to form a tube and form a loop with neighboring proliferating sites. The basal membrane develops on the newly formed vessels. This process is subject to control through mediators that antagonize one another. Among the angiogenesis-stinulating factors is the acidic fibroblast growth factor (FGF-1), the basic fibroblast growth factor (FGF-2), the vascular endothelial growth factor (VEGF), interleukin 1 $\alpha$ (IL 1$\alpha$), and others. Endogenous inhibitors confront these stimulating factors and in a healthy person prevent angiogenesis.

The neoformation of vessels plays a role in the pathogenesis of various diseases. Among these above all are tumor diseases. Both the growth of a solid tumor as well as its metastasis are dependent on angiogenesis in the tumor tissue. Other important examples of diseases in which angiogenesis plays a pathogenetic role have already been mentioned above.

Effective and low side effect angiogenesis inhibitors today still represent a therapeutic gap, since there are still no angiogenesis inhibitors available that are permitted for human use. Various angiogenesis inhibitors, for example, Sumarin, have been clinically tested, but their therapeutic use is questionable because of toxic effects.

With the pharmacological testing of the lyophilizate of the primary tincture of *Alchemilla vulgaris* on the CAM of chicken embryos there appeared, completely surprisingly, the strong angiogenesis-inhibiting effect of a plant-based drug, for which no side effects have become known up to now.

New therapeutic strategies in cases of rheumatoid arthritis are being sought in angiogenesis inhibitors, since in the inflammation process the synovial proliferation is connected with a neovascularization. Suppression of the proliferation of endothelial cells can be seen as an important therapeutic goal, since with this one can also expect a reduction of the pathological/immunological process.

Tolerable average doses of the *Herba Alchemille* in phytotherapy go as high as 10 g, but cannot be seen as a maximum dosage. Therefore, possible dosages of the primary tincture dry substance are preferably between 20 mg and 2 g.

Dragées, hard gelatin capsules, liquid preparations of the primary tincture dry substance as oral medicines, topical drugs or injectable drugs may be considered as administration forms.

The features of the invention disclosed in this description and in the claims can be important both individually and in any combination for the realization of the invention in its various embodiments.

What is claimed is:

1. A metbod for inhibiting angiogenesis, comprising administering to a patient in need thereof an extract of *Alchemilla vulgaris* in an effective amount to inhibit angiogenesis, wherein the extract of *Alchemilla vulgaris* comprises a primary tincture.

2. The method of claim 1 wherein the extract of *Alchemilla vulgaris* is a lyophilizate.

3. The method of claim 1, wherein the angiogenesis is associated with a tumor disease, rheumatoid arthritis or other chronic inflammatory disease, psoriasis, retinopathy, or periodontal inflammation.

4. The method of claim 1, wherein the primary tincture is a dried primary tincture.

5. The method of claim 4, wherein the dried primary tincture is administered at a dosage between 20 mg and 2 g per day.

6. The method of claim 4, wherein the dried primary tincture is administered as a dragée, hard gelatin capsule or liquid preparation.

7. The method of claim 4, wherein the dried primary tincture is administered orally, topically, or by injection.

8. A method for inhibiting angiogenesis, comprising administering to a patient in need thereof an alcoholic extract of *Alchemilla vulgaris* in an amount effective to inhibit angiogenesis.

9. The method of claim 8 wherein the extract of *Alchemilla vulgaris* is a lyophilizate.

10. The method of claim 8, wherein the angiogenesis is associated with a tumor disease, rheumatoid arthritis or other chronic inflammatory disease, psoriasis, retinopathy, or periodontal inflammation.

11. The method of claim 8, wherein the extract is a primary tincture.

12. The method of claim 11, wherein the primary tincture is a dried primary tincture.

13. The method of claim 12, wherein the dried prime tincture is administered at a dosage between 20 mg and 2 g per day.

14. The method of claim 12, wherein the dried primary tincture is administered as a dragée, hard gelatin capsule or liquid preparation.

15. The method of claim 11, wherein the dried primary tincture is administered orally, topically, or by injection.

16. The method of claim 8, wherein the alcoholic extract is an ethanol extract.

17. The method of claim 16, wherein the ethanol extract is a 43% (w/w) ethanol extract.

18. The method of claim 8, wherein administration of the alcoholic extract includes at least one of oral administration, topical administration, or administration by injection.

* * * * *

UNITED STATES PATENT AND TRADEMARK OFFICE
CERTIFICATE OF CORRECTION

PATENT NO. : 6,395,309 B1  Page 1 of 1
DATED : May 28, 2002
INVENTOR(S) : Gerhard Franz and Dietrich H. Paper It is certified that error appears in the above-identified patent and that said Letters Patent is hereby corrected as shown below:

<u>Title page,</u>
Item [30], Foreign Application Priority Data, delete "Mar. 25, 1998" and insert -- Mar. 26, 1997 --, therefor.

Signed and Sealed this

Twenty-fifth Day of March, 2003

JAMES E. ROGAN
*Director of the United States Patent and Trademark Office*